United States Patent [19]

Brennan et al.

[11] Patent Number: 4,547,591
[45] Date of Patent: Oct. 15, 1985

[54] PREPARATION OF LINEAR POLYETHYLENEPOLYAMINES WITH SILICA-ALUMINA CATALYSTS

[75] Inventors: Michael E. Brennan; James H. Templeton; Ernest L. Yeakey, all of Austin, Tex.

[73] Assignee: Texaco Inc., White Plains, N.Y.

[21] Appl. No.: 562,122

[22] Filed: Dec. 16, 1983

[51] Int. Cl.$^4$ .............................................. C07C 85/06
[52] U.S. Cl. ................... 564/479; 564/469; 564/470; 564/512
[58] Field of Search ............... 564/479, 512, 470, 469

[56] References Cited

U.S. PATENT DOCUMENTS 2,574,693  11/1951  Engel et al. ...................... 564/469
4,036,881  7/1977  Brennan et al. ...................... 564/479

FOREIGN PATENT DOCUMENTS 55-38329  3/1980  Japan ...................... 564/479

Primary Examiner—Charles F. Warren
Assistant Examiner—John A. Sopp
Attorney, Agent, or Firm—Jack H. Park; Kenneth R. Priem; Harold J. Delhommer

[57] ABSTRACT

Disclosed is a process for preparing predominantly linear polyethylenepolyamines from the catalyzed reaction of (1) an ethyleneamine and an alkanolamine, (2) ethyleneamines or (3) an alkanolamine and ammonia. The catalyst employed is a silica-alumina catalyst. An acidic phosphorus cocatalyst may be used in conjunction with the silica-alumina catalyst.

4 Claims, No Drawings

PREPARATION OF LINEAR POLYETHYLENEPOLYAMINES WITH SILICA-ALUMINA CATALYSTS

BACKGROUND OF THE INVENTION

This invention relates to a novel use of silica-alumina catalysts in the preparation of predominantly linear polyethylenepolyamines from ethyleneamines and alkanolamines.

Heretofore, polyethylenepolyamine compounds such as diethylenetriamine, triethylenetetramine and the higher homologs have been produced by the reaction of an alkyl halide such as ethylene dichloride with an amine such as ammonia or ethylenediamine at elevated temperatures and pressures. Normally, relatively high yields of predominently noncyclic polyethylenepolyamine compounds are obtained from this process with varying yields of heterocyclic amines.

The large amounts of energy required to produce the reactants as well as the difficult separation procedures required to recover the more valuable linear polyethylenepolyamines diminish the usefulness of the ethylene dichloride process. The hydrohalide salts of ammonia and the polyethylenepolyamine products must also undergo difficult and time consuming caustic neutralization to yield the free polyethylenepolyamines.

Another method of producing predominantly linear polyethylenepolyamines is exemplified by U.S. Pat. Nos. 4,316,840 and 4,316,841. These two references disclose a method of contacting a polyalkylenepolyamine such as ethylenediamine with water in the presence of several different catalysts. The suggested catalysts of U.S. Pat. No. 4,316,841 are various metal phosphates including boron phosphate, iron phosphate, zinc phosphate, aluminum phosphate and others. U.S. Pat. No. 4,316,840 discloses the use of various metal sulphates and nitrates as catalysts instead of metal phoshpates.

A third method of producing predominantly linear polyalkylenepolyamines is disclosed in U.S. Pat. Nos. 4,036,881; 4,044,053; 4,103,087 and 4,314,083. These four references describe a method of reacting an alkyleneamine such as ethylenediamine with an alkanolamine such as monoethanolamine. U.S. Pat. Nos. 4,036,881 and 4,044,053 discloses the use of a phosphorus-containing catalyst such as an acidic metal phosphate, phosphoric acid compounds, phosphorous acid compounds, and various other phosphate esters, acids and salts. The preferred catalysts of the disclosures are the acidic metal phosphates including boron phosphate, ferric phosphate and aluminum phosphate. Additionally, the process of '881 yields a relatively lower conversion to linear polyethylenepolyamines when the disclosed catalyst is employed rather than the supported catalyst prepared according to the present invention.

Additional references which describe the alkyleneamine and alkanolamine reaction with a catalyst are U.S. Pat. Nos. 4,103,087 and 4,314,083. U.S. Pat. No. 4,103,087 provides an example of a specific aluminum phosphate catalyst employed for producing heterocyclic product compounds. The use of metal salts of nitrogen and sulfur-containing compounds and their corresponding acids is described in U.S. Pat. No. 4,314,083 to catalyze the reaction between ethylenediamine and monoethanolamine.

U.K. Pat. Nos. 2,090,157; 2,090,158; 2,090,238; 2,090,267 and 2,090,268 all disclose the use of various catalyst supports containing phosphorus compounds for the polymerization of olefins. More particularly, U.K. Pat. No. 2,090,158 claims a chromium compound supported on a silica and metal phosphate combination wherein the support is prepared by impregnating a silica xerogel with aluminum phosphate or boron phosphate and then precipitating aluminum phosphate on the support in the presence of a silica hydrogel. U.K. Pat. No. 2,090,267 describes a catalyst of a chromium compound on a phosphate-containing support, the support of which can be made by phosphating silica. A method of preparing aluminum phosphate gels as supports for olefin polymerization catalysts is disclosed in U.K. Pat. No. 2,090,238. Chromium compounds supported on aluminum phosphate or a phosphate containing support are claimed in U.K. Pat. No. 2,090,268.

SUMMARY OF THE INVENTION

A novel method of using a silica-alumina catalyst is disclosed herein to produce predominantly linear polyethylenepolyamines from several sets of reactants including (1) an ethyleneamine and an alkanolamine; (2) ethyleneamines; and (3) an alkanolamine and ammonia. An acidic phosphorus cocatalyst may also be used in conjunction with the silica-alumina catalyst.

DETAILED DESCRIPTION

The invention is a method of reacting (1) ethyleneamines and alkanolamines, (2) reacting ethyleneamines or (3) reacting an alkanolamine with ammonia catalyzed by a silica-alumina catalyst to produce predominantly linear polyethylenepolyamines such as diethylenetriamine, triethylenetetramine, tetraethylenepentamine and pentaethylenehexamine. The high selectivity of the catalyst towards linear polyethylenepolyamines is in direct contrast to the product selectivities of much of the prior art catalysts toward the less valuable heterocyclic polyamines. The linear polyethylenepolyamines are particularly useful as chemical intermediates to produce other compounds and are also employed in the manufacture of various adhesive formulations.

The silica-alumina catalyst catalyzes the reaction of (1) alkyleneamines and alkanolamines, preferably ethylenediamine and monoethanolamine, (2) ethyleneamines and (3) alkanolamines and ammonia at a temperature of from about 250° C. to about 400° C. and a pressure of about 500 to about 5000 psig, preferably from about 275° C. to about 325° C., and a pressure of about 1000 to about 3000 psig. The molar ratio of preferred reactants ethylenediamine to monoethanolamine ranges from about 1:2 to about 5:1, preferably from about 1 to about 2 moles of ethylenediamine per mole of monoethanolamine. It should be noted that other alkyleneamines besides ethylenediamine may be used in the catalyzed reaction of the present invention. Produced products from the catalyzed reaction may further react with the initial starting reagents to ultimately produce higher molecular weight polyalkylenepolyamines. For the ammonia/alkanolamine reaction, a molar ratio of about 2/1 to about 10/1 is employed.

The silica-alumina catalysts used in the invention method contain about 50% to about 90% silica and from about 5% to about 50% alumina by weight. Silica-alumina catalysts which have been successfully employed in the practice of the invention include: Aerocat ® triple alumina (25% $Al_2O_3$), a tradmarked product sold by American Cyanamid Company; HSA- 300 (159CP-85, 12.4% $Al_2O_3$ with about 290-315$M^2$/gm surface area); T-1219, a trademarked silica-alumina sold by United Catalysts, Inc. (UCI); K-306, a trademarked montmorillonite acid clay sold by United Catalysts, Inc.; Superfiltrol acid clay (Grade 1), a trademarked product sold by Filtrol Corp.; and multiple grades of Davison silica-alumina (Grade 979 with 13% $Al_2O_3$ and 400 $m^2$/gm surface area), (Grade 980-25 with 25% $Al_2O_3$ and 325 $m^2$/gm surface area), (Grade 970 with 13% $Al_2O_3$ and 100 $m^2$/gm surface area), trademarked products sold by the Davison Chemical Division of W. R. Grace & Co.

The quantity of silica-alumina catalyst employed in the invention is an effective amount which can vary widely depending upon the reactivity desired, the reactants present and the particular reaction conditions employed. The catalytically effective amount for a batch process is within the range of from about 0.01 to about 20.0 weight percent, based upon the weight of the preferred monoethanolamine reactant present before reaction. Preferably, the silica-alumina catalyst is employed in an amount ranging from about 2.5 to about 6.0 weight percent, monoethanolamine basis.

About 0.1% to about 3.0% by weight of acidic phosphorus cocatalyst (based on the amount of alkanolamine present) may also be employed with the silica-alumina catalyst in the practice of the invention. An acidic phosphorus cocatalyst has a synergistic effect on the catalyzed reaction and generally increases product yield. Phosphorous acid ($H_3PO_3$) is the preferred cocatalyst.

The process of the present invention can be practiced batch-wise or in a continuous manner. When a batch process is to be utilized, the catalyst, in particulate or pelleted form, is slurried with the ethyleneamine and alkanolamine in any suitable reactor such as a stirred, jacketed autoclave where the desired reaction conditions can be maintained.

The reaction is more preferably conducted in a continuous fashion by passing the ethyleneamine, alkanolamine and recycle, if any, through a reaction zone containing the catalyst of the present invention in pelleted form. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence, a desired percentage of conversion of the reactants. For example, a higher reaction temperature may require a lower reaction time. Furthermore, in a continuous process, it is not necessary to drive the reaction to completion because unreacted feedstock components can be recycled to the reactor.

It is preferred to use cylindrically-shaped silica-alumina catalyst pellets having a diameter essentially equal to the length thereof, such as diameters and lengths ranging from about 1/32" to about ⅜". It will be understood that the shape and dimensions of the pellets are not critical to the present invention and that pellets of any suitable shape and size may be used by one wishing to practice the present invention.

When cylindrical pellets of catalyst of the type described above are used, the weighted hourly space velocity may be varied within wide limits (e.g., 0.1 to 10 weight of feed/hour/volume of catalyst) to obtain a desired rate of conversion, as explained above. But a space velocity of about 0.35 to about 5 is preferred.

When a continuous process is employed, it is important that the catalyst pellets maintain their integrity under the reaction conditions that are employed. Otherwise, the economics of the catalyzed process become unfavorable. If the pellets are easily crushed or if the harsh chemical environment causes them to disintegrate, the yield will be adversely affected and, in extreme cases, reactor plugging may occur. It is a feature of the present invention that the pelleted catalyst compositions have improved resistance to physical degradation when used to catalyze the reaction of ethyleneamines with alkanolamines or ethyleneamines with ethyleneamines.

There are many compounds which can be formed from the reactions of ethyleneamines and alkanolamines and ethyleneamines with ethyleneamines besides the preferred linear polyethylenepolyamines such as diethylenetriamine, triethylenetetramine, tetraethylenepentamine and pentaethylenehexamine. Less desirable cyclic compounds such as piperazine and N-(2-aminoethyl)piperazine, are also formed.

In most cases, the more desired linear polyethylenepolyamines can be recovered from the reaction product mixture by conventional methods such as distillation. Such distillation recovery methods are well known in the art. One exception is a group of compounds that have similar distillation properties to triethylenetetramine. The cyclic compounds of diaminoethylpiperazine and piperazinoethylethylenediamine as well as the linear compound nitrilotrisethylamine are very difficult, if not impossible, to separate from triethylenetetramine by distillation. Thus, a process which produces a high percentage of noncylic compounds in the triethylenetetramine range is more desirable than a process which produces a lower percentage of noncyclic compounds in the triethylenetetramine distillation range.

An advantage of the claimed invention is that the polyethylenepolyamines produced and recovered from the reaction mixture can be further reacted with the initial ethyleneamine or alkanolamine reactants to produce a larger percentage of the higher molecular weight linear polyethylenepolyamines. Diethylenetriamine, triethylenetetramine, tetraethylenepentamine and N-(2-aminoethyl)ethanolamine can all be recycled and substituted for some or all of the initial ethylenediamine reactants to improve the yield of higher molecular weight polyethylenepolyamines. However, the recycling of N-(2-aminoethyl)ethanolamine would also yield a higher percentage of piperazine, a cyclic compound. This shift in product selectivities to the higher molecular weight polyethylenepolyamines by recycling produced products forms an added advantage of the instant process.

The following examples will further illustrate the preparation of predominantly linear polyethylenepolyamines from ethyleneamines and alkanolamines by the use of the silica-alumina catalyst with or without the optional acidic phosphorus cocatalsyt. They are given by way of illustration and not as limitations on the scope of the invention. Thus, it will be understood that reactants, proportions of reactants, and time, temperature and pressure of the reaction steps may be varied with much the same results achieved.

For purposes of convenience and brevity, the reactant compounds employed, the products obtained and other terms have been abbreviated in the following examples and tables. The abbreviations employed are:

EDA—ethylenediamine
MEA—monoethanolamine

DETA—diethylenetriamine
TETA—triethylenetetramine
TEPA—tetraethylenepentamine
PEHA—pentaethylenehexamine
AEEA—N-(2-aminoethyl)ethanolamine
AEP—N-(2-aminoethyl)piperazine
DiAEP—diaminoethylpiperazine
PEEDA—piperazinoethylethylenediamine
NTEA—nitrilotrisethylamine
PIP—piperazine
HEP—N-(2-hydroxyethyl)piperazine
SV—space velocity
GLC A%—gas liquid chromatography area %
% P Rec.—phosphorus recovery
% NC—percent noncyclic
t—trace

EXAMPLES 1-6

In Example 1, a solution of MEA (305.4 gm, 5.0 moles) and EDA (150.2 gm, 2.5 moles) and 15.3 gm (5.0 wt. %, basis MEA) Aerocat ® triple alumina (25.0% Al₂O₃) catalyst was charged to a clean, dry, nitrogen purged, 1 liter stirred autoclave. After padding with nitrogen, the autoclave was heated to 300° C. over a period of one hour and 25 minutes and then held at 300° C. for an additional two hours. Pressure increased from 382 to 490 psig at the reaction temperature. After cooling the reaction mixture to ambient temperature and venting, 95.6% of the charge was recovered.

Gas liquid chromatography analysis indicated that conversions were 5.8% EDA and 8.2% MEA, giving 7.3% total conversion as indicated in Table 1. The product analyzed by gas liquid chromatrography had a trace of piperazine, 58.5% DETA, 1.9 AEP, 37.7% AEEA+HEP and 1.9% unknown.

Experiment 1 was repeated at different EDA/MEA ratios and different temperatures and pressures in Examples 2-6. Examples 2, 3 and 6 gave the largest quantities of the higher molecular weight linear polyethylenepolyamine such as TETA, TEPA and PEHA, although these results were achieved at the price of proportionately less DETA. However, Examples 2, 3 and 6 gave drastically higher conversions of reactants to products at their higher temperatures and pressures and thus, gave much greater quantities of DETA, although the DETA proportion of the product was less.

It should be noted that total product yield as reflected by the percent total conversion increased dramatically as reaction temperature and reaction pressure also increased. Higher reaction temperature and pressure also produced more cyclics such as piperazine and AEP at the same time as producing the higher molecular weight, linear polyethylenepolyamines.

EXAMPLES 7-11

Results similar to Examples 1-6 were noticed in Examples 7-11 (Table 2) which were performed with a different silica-alumina catalyst, Superfiltrol acid clay (grade 1). As in the previous examples, the catalyst was used in the amount of 5.0 wt. %, basis MEA for two hours. The same tradeoff discovered in the first examples was also present with this silica-alumina catalyst. As reaction temperature and pressure increased, product yield increased dramatically. But, cyclic production increased along with the production of the valuable, higher molecular weight, linear polyethylenepolyamines. If it is desired to produce a high percentage of DETA alone, one would choose a relatively lower reaction temperature of 300° C. and a lower pressure of about 500 psig such as in Example 11 to produce only traces of cyclic compounds and have a product that is almost exclusively DETA. However, the extremely small product yield of Example 11 makes the process of Example 11 impractical. On the other hand, the reaction conditions of Example 9 produced exceptionally high amounts of TETA, TEPA and PEHA with an extremely high product yield of 84%.

EXAMPLES 12-16

Examples 12-16 represent test runs of several different silica-alumina catalysts. The results are shown in Table 3. In Examples 12 and 13, the HSA-300 catalyst containing 12.4% alumina sold by Houdry performed substantially better than the other catalyst. A 27% conversion to the product was obtained at a temperature of 314° C. Additionally, substantial quantities of TETA, TEPA, and PEHA were produced with a substantially lower piperazine production than the other catalyst. Under these reaction conditions, the two Girdler catalysts of Examples 14 and 15 produced undesirable results.

A control run with no catalyst present for the EDA/MEA ratio of 1.0 at 300° C. for two hours gave a total conversion of product of only 1.0%. This demonstrates the substantial catalystic activity provided by the silica-alumina catalysts.

EXAMPLES 17-24

The Aerocat ® triple alumina catalyst was tried under several different reaction conditions along with three runs for the Superfiltrol acid clay catalyst, the HSA-300 catalyst and the Girdler T-1219 catalyst. The results listed in Table 4 of these experimental runs confirmed that a relatively higher reaction temperature produces substantially greater conversion to products. Higher pressure also increases product yield but not to the same degree as an increased temperature. At the same time, higher temperatures and product yields result in greater amounts of cyclic compounds in the product. The reactions with relatively smaller quantities of products also produce much purer noncyclic products. Cyclic production is generally very low when product yield is low.

Examples 17, 19 and 20 provide excellent illustrations of the above-stated guidelines. Product yield increased from 8% to 40% from Example 17 to 19 as the reaction conditions increased from 300° C. and 730 psig to 325° C. and 3000 psig. At the same time, cyclic production, indicated generally as PIP and AEP, increased from negligible amounts of about 2% all the way to 34% of the product. The product in Example 17 was DETA of a high purity. But in Example 19, the production of cyclics and the higher molecular weight, linear polyethylenepolyamines significantly increased.

Under the changed reaction conditions of Example 20, wherein the temperature was increased 13° C. and the reaction pressure was decreased to 2600 psig from the 3000 psig of Example 19, product yield increased from 40% to 45% and cyclic production also decreased. Noncyclic TETA production increased to 74%. Noncyclic TETA production is an important guidepost because it is very difficult to separate cyclic TETA class compounds from noncyclic TETA compounds. Thus, it is highly desirable to have a relatively large percentage of noncyclic TETA compounds. Example 22 also produced fine results in that cyclic production was very low, and TETA production was composed of 88.4% noncyclic TETA compounds.

EXAMPLES 25-32

Table 5 lists the results for Examples 25-32 wherein the EDA/MEA condensation reaction was conducted over the HSA-300 silica-alumina catalyst (159CP-85, 12.4% $Al_2O_3$ with 290-315 square meters per gram of surface area in the form of 5/32 by 5/32 inch tablets). In Examples 27 through 32, the HSA-300 silica-alumina catalyst was also joined by a phosphorous acid cocatalyst in varying amounts.

Examples 25, 27 and 29 are most instructive. Examples 27 and 29 illustrate relatively higher product yields, increased DETA to piperazine ratios, as well as a greater percentage of noncyclic TETA compounds. Thus, Examples 27 and 29 illustrate the added synergistic benefit of having a phosphorous acid cocatalyst used in conjunction with the HSA-300 silica-alumina catalyst. Example 29 is particularly instructive as it is the average of eight different samples taken over 101 hour test run. The ratio of noncyclic DETA to cyclic piperazine is a very high number of 6.5.

Examples 31 and 32 illustrate that the addition of 15% to 30% water with the feed produced less desirable products. All runs were performed at 1500 psig.

EXAMPLES 33-34

Table 6 shows the results of runs where two different catalyst, the Aerocat ® triple alumina and the Superfiltrol acid clay were employed to catalyze the self reaction of DETA with itself at 300° to 305° C. and 425 to 585 psig for two hours in the presence of about 5.0% catalyst. 80% grade DETA was used.

The Superfiltrol acid clay catalyst used in Example 34 gave excellent results that were substantially better than the results achieved with the Aerocat ® silica-alumina catalyst. Cyclic production was decreased by one third and production of the valuable TETA, TEPA and PEHA compounds was increased by about 15%. The doubling of product yield with the Superfiltrol silica-alumina catalyst made these differences even greater.

EXAMPLES 35-42

Table 7 lists the results for Examples 35-42 which analyzed the reaction of MEA and ammonia to produce ethylenediamine and higher polyethylenepolyamines. $NH_3$/MEA mole ratios of about 3 to 4 were employed in the presence of the HSA-300 silica-alumina catalyst by itself or with phosphorous acid as a cocatalyst and/or hydrogen at 2600 psig. The results of Examples 39-42 gave better product conversions when the phosphorous acid cocatalyst was used with the silica-alumina catalyst. Example 39 gave unusual results. If it is assumed that something was wrong with the results of Example 39, it can be concluded that the presence of hydrogen decreased product yield as well as the amount of noncyclic TETA compounds.

EXAMPLES 43-48

Table 8 lists the results for Examples 43-48 which illustrated the reaction of various mole ratios of $NH_3$/MEA at 300° C. and 2600 psig over the Davison (Grade 979) silica-alumina catalyst by itself and in the presence of phosphorous acid as a cocatalyst. Several runs were conducted with the $NH_3$/MEA molar ratio in the 3 to 4 range and at 7 and 10. Generally, the runs with phosphorous acid as a cocatalyst along with the Davison silica-alumina catalyst gave the best results.

EXAMPLES 49-53

Table 9 lists the results for Examples 40-53 obtained for the EDA/MEA reaction in the presence of the Davison silica-alumina catalyst (Grade 979, 13% $Al_2O_3$, 3/16 inch extrusions with a surface area of 400 square meters per gram). Phosphorous acid cocatalyst was also added in Examples 51-53 to deliver improved product yields. Example 53 was a continuous six day run that included a daily water wash to remove deposited phosphorus compounds. Pressure was 1500 psig for all runs.

EXAMPLES 54-57

Table 10 lists the results for Examples 54-57 for the EDA/MEA condensation reaction at 1500 psig over the Davison silica-alumina catalyst (Grade 980-25, 25% $Al_2O_3$ and 325 square meters per gram surface area) by itself and in the presence of phosphorous acid.

These examples further support the reaction condition guidelines of the previous examples that better results are achieved when the silica-alumina catalyst is used with the cocatalyst of phosphorous acid. In addition, better results were achieved at 300° C. as opposed to 325° C. at the 1500 psig reaction conditions these examples were run under. Examples 54 and 56 achieved outstanding ratios of DETA/PIP of 12 to 13 and outstanding percentages of noncyclic TETA of 100% and 97.4%. Such results in a commercial process would eliminate the necessity for separating out cyclic compounds from the product. When the phosphorous acid cocatalyst was employed along with the silica-alumina catalyst, total product yield almost doubled from Example 54 to Example 56 under much the same reaction conditions.

EXAMPLES 58-67

Table 11 lists the results for Examples 58-67 and compares the catalysis provided by several different grades of the Davison silica-alumina catalyst as well as two different grades of the United Catalysts, Inc. silica-alumina catalyst. Reaction conditions were EDA/MEA mole ratio of 1.0, 1500 psig and 300° and 325° C. for each different catalyst. In every case, product yield showed a 100% to 150% increase when reaction temperature was raised only 25° C. from 300° C. to 325° C. However, the increase of 25° C. in reaction temperature drastically lowered the DETA/PIP ratio as well as decreasing substantially, in some cases by more than 50%, the percent noncyclic TETA compounds produced. Thus, it can be concluded that the small increase in reaction temperature generally doubled the product yield at the cost of substantially greater amounts of undesirable cyclic compounds.

EXAMPLES 68-74

The Davison silica-alumina catalyst (grade 980-25) was further scrutinized with respect to temperature, space velocity and mole ratio of EDA/MEA. The reactions were carried out with the silica-alumina catalyst at 1500 psig. The results in Table 12 indicate that the correlations previously noted between temperature, product yield, and amount of cyclic compounds in the product also held true with these examples. As temperature increased, product yield increased along with an increased production of cyclic compounds.

EXAMPLES 75-77

The Davison silica-alumina catalyst (grade 980-25) which had been used in several previous EDA/MEA and MEA/NH$_3$ reaction was subjected again to several standard run conditions for long periods of time to test catalyst aging. Table 13 lists the results for three runs which showed that the aged catalyst was considerably deactivated, giving about half the product yield as the catalyst with only 18 hours of age. However, the percentage of cyclic compounds produced was substantially decreased. The 150 hour catalysts had very high DETA/PIP ratios of 10 to 12 and 92% to 94% noncyclic TETA compounds as opposed to a DETA/PIP ratio of 3 and 68% noncyclic TETA compounds with the 18 hour catalyst.

Many other variations and modifications may be made in the concepts described above by those skilled in the art without departing from the concepts of the present invention. Accordingly, it should be clearly understood that the concepts disclosed in the description are illustrative only and are not intended as limitations on the scope of the invention.

TABLE 1

| Ex. | EDA/MEA (moles) (1) | Temp., °C. | Max. Press., psig | % Total conv. | GLC A % (Lts., H$_2$O, reactants free) | | | | | |
|---|---|---|---|---|---|---|---|---|---|---|
| | | | | | PIP | DETA | AEEA/HEP | AEP | TETA | TEPA | PEHA |
| 1 | 0.5 | 300 | 490 | 7.3 | t | 58.5 | 37.7 | 1.9 | — | — | — |
| 2 | 0.5 | 325 | 1060 | 27.6 | 16.0 | 31.5 | 32.0 | 3.6 | 14.1 | 2.3 | — |
| 3 | 0.5 | 350 | 2600 | 57.2 | 9.0 | 22.0 | — | 15.4 | 11.4 | 4.5 | 3.5 |
| 4 | 1.0 | 300 | 500 | 4.2 | t | 75.0 | 25.0 | — | — | — | — |
| 5 | 2.0 | 300 | 560 | 2.2 | t | 86.7 | 13.3 | — | — | — | — |
| 6 | 2.8 | 335 | 1450 | 28.0 | 7.6 | 55.6 | 7.8 | 3.6 | 18.3 | 3.2 | — |

(1) Reaction in the presence of 5.0 wt % Aerocat ® TA catalyst (MEA basis).

TABLE 2

| Ex. | EDA/MEA (moles) (1) | Temp., °C. | Max. Press., psig | % Total conv. | GLC A % (Lts., H$_2$O, reactants free) | | | | | |
|---|---|---|---|---|---|---|---|---|---|---|
| | | | | | PIP | DETA | AEEA/HEP | AEP | TETA | TEPA | PEHA |
| 7 | 0.5 | 300 | 505 | 4.2 | t | 61.3 | 38.7 | — | — | — | — |
| 8 | 0.5 | 325 | 1000 | 25.0 | 9.5 | 22.3 | 35.0 | | 20.9 | 1.4 | — |
| 9 | 0.5 | 350 | 2950 | 84.1 | 8.6 | 1.2 | 12.0 | 12.0 | 17.0 | 12.4 | 18.2 |
| 10 | 1.0 | 300 | 510 | 3.0 | t | 73.7 | 26.3 | — | — | — | — |
| 11 | 2.0 | 300 | 510 | 1.4 | t | 87.5 | 12.5 | — | — | — | — |

(1) Reaction in the presence of 5.0 wt % Superfiltrol acid clay catalyst (MEA basis).

TABLE 3

| Ex. | EDA/MEA (moles) | Catalyst 5% by wt. | Temp., °C. | Max Press., psig | % Total Conv. | GLC A % (Lts., H$_2$O, reactants free) | | | | | | |
|---|---|---|---|---|---|---|---|---|---|---|---|---|
| | | | | | | PIP | DETA | AEEA | AEP-HEP | TETA | TEPA | PEHA |
| 12 | 1.0 | HSA-300$^{(1)}$ | 314 | 2400 | 26.9 | 8.9 | 26.8 | 11.5 | 11.2 | 7.8 | 1.5 | — |
| 13 | 1.0 | HSA-300 | 300 | 760 | 9.0 | 7.5 | 53.1 | 23.2 | 3.7 | 5.0 | 1.7 | 3.5 |
| 14 | 1.0 | T-1219$^{(2)}$ | 300 | 670 | 1.2 | 22.2 | 77.8 | — | — | — | — | — |
| 15 | 1.0 | K-306$^{(3)}$ | 300 | 670 | 3.7 | 23.5 | 73.6 | — | 2.9 | — | — | — |
| 16 | 1.0 | E-25$^{(4)}$ | 315 | 725 | 13.9 | 3.4 | 53.8 | 32.5 | 1.7 | — | — | — |

$^{(1)}$Houdry silica-alumina (159CP-85, 12.4% Al$_2$O$_3$)
$^{(2)}$UCI silica-alumina
$^{(3)}$UCI montmorillonite acid clay
$^{(4)}$American Cyanamid extruded Aerocat ® TA (25.0% Al$_2$O$_3$)

TABLE 4

| Ex. | Catalyst 5% by wt. | Temp., °C. | Press., psig. | % EDA conv. | GLC A % (NH$_3$, EDA free) | | | | | |
|---|---|---|---|---|---|---|---|---|---|---|
| | | | | | PIP | DETA | AEP | TETA | TEPA | PEHA |
| 17 | A$^{(1)}$ | 300 | 730 | 7.9 | 1.7 | 89.7 | — | — | — | — |
| 18 | S$^{(2)}$ | 300 | 690 | 6.9 | 2.0 | 98.0 | — | — | — | — |
| 19 | A | 325 | 3000 | 40.4 | 25.7 | 38.1 | 8.8 | 15.4$^{(3)}$ | 1.6 | 1.9 |
| 20 | A | 338 | 2600 | 44.9 | 13.7 | 42.3 | 7.7 | 18.7$^{(4)}$ | 4.1 | 1.0 |
| 21 | A$^{(5)}$ | 335 | 1650 | 16.9 | 5.8 | 73.8 | 1.2 | 11.0 | 0.6 | — |
| 22 | A$^{(5)}$ | 335 | 1775 | 21.8 | 6.8 | 69.4 | 1.6 | 13.5$^{(8)}$ | 1.0 | — |
| 23 | HSA-300$^{(6)}$ | 325 | 1175 | 15.4 | 3.9 | 88.2 | — | 6.3 | — | 0.8 |
| 24 | T-1219$^{(7)}$ | 325 | 1000 | 0.2 | — | — | 100.0 | — | — | — |

$^{(1)}$Aerocat ® TA (25% Al$_2$O$_3$).
$^{(2)}$Superfiltrol acid clay (grade 1).
$^{(3)}$10.2% NTEA, 38.8 TETA, 12.3 Unknowns (2), 18.4 DiAEP, 20.4 PEEDA.
$^{(4)}$1.3% NTEA, 73.1 TETA, 6.4 Unknowns (2), 3.8 DiAEP, 15.4 PEEDA.
$^{(5)}$91% EDA feed.
$^{(6)}$Houdry silica-alumina (HSA-300, 159CP-85, 12.4% Al$_2$O$_3$).
$^{(7)}$UCI silica-alumina.
$^{(8)}$88.4% noncyclic.

TABLE 5

| Ex. | EDA/MEA (moles) | HSA-300 Catalyst and ..., wt. % | Temp., °C. | SV | % Total Conv. | DETA PIP | % NC, TETA | % P Rec., Eff. |
|---|---|---|---|---|---|---|---|---|
| 25 | 1.00 | — | 300 | 0.47 | 37.1[1] | 2.8 | 59.6 | — |
| 26 | 1.00 | — | 325 | 0.45 | 50.8 | 0.9 | 32.4 | — |
| 27 | 1.01 | $H_3PO_3$, 0.45 | 300 | 0.48 | 52.8[2] | 3.9 | 90.0 | 19.0 |
| 28 | 0.99 | $H_3PO_3$, 0.46 | 325 | 0.49 | 76.6 | 2.0 | 46.9 | 11.8 |
| 29 | 1.04[3] | $H_3PO_3$, 0.45 | 300 | 0.52 | 56.6 | 6.5 | 63.0 | 27.8 |
| 30 | 1.02 | $H_3PO_3$, 0.13 | 300 | 0.48 | 49.3 | 3.8 | 49.6 | 78.8 |
| 31 | 1.00[4] | $H_3PO_3$, 0.40 | 325 | 0.47 | 46.5 | 3.2 | 47.2 | 52.6 |
| 32 | 1.00[5] | $H_3PO_3$, 0.33 | 325 | 0.52 | 30.2 | 3.0 | 38.4 | 12.1 |

[1]Products, % yield: 10.8 piperazine, 30.5 DETA, 19.2 AEEA, 9.6 AEP/HEP, 21.4 TETA, 4.4 TEPA, 0.4 PEHA.
[2]Products, % yield: 11.9 piperazine, 46.1 DETA, 1.5 AEEA, 7.7 AEP/HEP, 23.9 TETA, 4.3 TEPA.
[3]101 hour test run and numbers listed are the average of 8 samples. Range: EDA/MEA, 0.88–1.28; SV, 0.48–0.59; % Total Conv., 52.2–60.9; DETA/PIP, 4.4–10.8; % NC TETA, 44.6–89.2; % P Rec., 23.6–35.4.
[4]Fresh catalyst and 15% water in feed.
[5]30% water in feed.

TABLE 6

| Ex. | Catalyst, 5 wt % | % DETA Conv. | GLC % (Lts., NH3DETA Free) | | | | |
|---|---|---|---|---|---|---|---|
| | | | PIP | AEP | TETA | TEPA | PEHA |
| 33 | Aerocat ® TA | 20.6 | 27.5 | 6.7 | 14.5 | 48.2 | 2.1 |
| 34 | Superfiltrol | 43.5 | 14.0 | 12.0 | 19.2 | 40.0 | 14.3 |

TABLE 7

| Ex. | HSA-300 Catalyst and ..., wt. % | $H_2$ | Temp., °C. | SV | % MEA Conv. | % EDA Yield | DETA PIP | % NC, TETA | % P Rec., Eff. |
|---|---|---|---|---|---|---|---|---|---|
| 35 | — | — | 300 | 0.52 | 35.5 | 35.3 | 0.6 | 27.5 | — |
| 36 | — | — | 325 | 0.52 | 50.2 | 27.8 | 0.2 | 0.0 | — |
| 37 | — | Yes | 300 | 0.48 | 23.5 | 32.5 | 4.0 | 0.0 | — |
| 38 | — | Yes | 325 | 0.52 | 58.5 | 23.3 | 0.2 | 0.0 | — |
| 39 | $H_3PO_3$, 0.46 | Yes | 300 | 0.50 | 63.4 | 31.4 | 1.8 | 46.9 | 1.7 |
| 40 | $H_3PO_3$, 0.47 | Yes | 325 | 0.52 | 84.6 | 21.6 | 1.2 | 16.6 | 2.0 |
| 41 | $H_3PO_3$, 0.46 | No | 300 | 0.48 | 40.1 | 40.4 | 1.5 | 37.1 | 1.7 |
| 42 | $H_3PO_3$, 0.46 | No | 325 | 0.55 | 67.8 | 30.6 | 2.1 | 35.6 | 1.4 |

TABLE 8

| Ex. | $NH_3$/MEA (moles) | Davison Catalyst (979) and ..., wt. % | SV | % MEA Conv. | % EDA Yield | DETA PIP | % NC, TETA | % P Rec., |
|---|---|---|---|---|---|---|---|---|
| 43 | 3.72 | — | 0.53 | 28.2 | 35.8 | 0.9 | 34.4 | — |
| 44 | 7.00 | — | 0.44 | 35.6 | 45.6 | 0.0 | 46.9 | — |
| 45 | 9.99 | — | 0.49 | 38.5 | 60.7 | <0.1 | — | — |
| 46 | 3.48 | $H_3PO_3$, 0.46 | 0.48 | 51.4 | 26.7 | 2.4 | 54.0 | 7.6 |
| 47 | 3.56[1] | $H_3PO_3$, 0.46 | 0.52 | 50.6 | 25.7 | 1.6 | 47.8 | 9.6 |
| 48 | 3.63[2] | $H_3PO_3$, 0.45 | 0.53 | 58.3 | 23.0 | 3.2 | 57.7 | 11.6 |

[1]75:25% $H_2$:$N_2$ present.
[2]$N_2$ present

TABLE 9

| Ex. | EDA/MEA (moles) | Davison Catalyst (979) and ..., wt % | Temp., °C. | SV | % Total Conv. | DETA PIP | % NC, TETA | % Rec., P |
|---|---|---|---|---|---|---|---|---|
| 49 | 1.00 | — | 300 | 0.49 | 34.2[1] | 3.1 | 78.6 | — |
| 50 | 1.00 | — | 325 | 0.53 | 47.2 | 1.0 | 28.4 | — |
| 51 | 0.81 | $H_3PO_3$, 0.54 | 300 | 0.50 | 44.2[2] | 8.5 | 89.2 | 25.8 |
| 52 | 0.89 | $H_3PO_3$, 0.51 | 325 | 0.49 | 59.5 | 4.8 | 66.4 | 17.8 |
| 53 | 0.78[3] | $H_3PO_3$, 0.53 | 300 | 0.56 | 62.5 | 4.8 | 60.6 | 9–46[4] |

[1]Products, A %: 11.3 piperazine, 34.9 DETA, 18.3 AEEA, 8.3 AEP/HEP, 18.6 TETA, 4.6 TEPA, 1.0 PEHA.
[2]Products, A %: 5.9 piperazine, 50.1 DETA, 4.4 AEEA, 6.6 AEP/HEP, 25.1 TETA, 4.9 TEPA, 1.2 PEHA.
[3]138 hour test run with intermittent water wash. Numbers listed are the average of 5 samples. Range: EDA/MEA, 0.56–1.08; wt. % $H_3PO_3$, 0.45–0.59; SV, 0.45–0.59, % Total Conv., 56.5–68.9; DETA/PIP, 2.2–6.1; % NC TETA, 30.6–81.5.
[4]Water washes removed from 17–27% of the deposited phosphorus.

TABLE 10

| Ex. | EDA/MEA (moles) | Davison Catalyst (980-25) and ..., wt. % | Temp., °C. | SV | % Total Conv. | DETA PIP | % NC, TETA | % Rec., P |
|---|---|---|---|---|---|---|---|---|
| 54 | 1.00 | — | 300 | 0.47 | 18.2 | 12.9 | 100.00 | — |

TABLE 10-continued

| Ex. | EDA/MEA (moles) | Davison Catalyst (980-25) and ..., wt. % | Temp., °C. | SV | % Total Conv. | DETA PIP | % NC, TETA | % Rec., P |
|---|---|---|---|---|---|---|---|---|
| 55 | 1.00 | — | 325 | 0.50 | 42.4[1] | 3.3 | 68.4 | — |
| 56 | 0.99 | $H_3PO_3$, 0.50 | 300 | 0.42 | 33.8 | 12.0 | 97.4 | 3.6 |
| 57 | 0.86 | $H_3PO_3$, 0.54 | 325 | 0.52 | 54.3[2] | 4.8 | 69.3 | 4.3 |

[1]Products, A %: 10.2 piperazine, 33.6 DETA, 7.8 AEEA, 10.2 AEP/HEP, 21.2 TETA, 6.7 TEPA, 3.8 PEHA.
[2]Products, A %: 8.8 piperazine, 42.3 DETA, 4.7 AEEA, 11.2 AEP/HEP, 19.8 TETA, 7.4 TEPA, 2.2 PEHA.

TABLE 11

| Ex. | Catalyst | % $Al_2O_3$ | SA $m^2$/gm | Temp., °C. | SV | % Total Conv. | DETA PIP | % NC, TETA | % AEEA |
|---|---|---|---|---|---|---|---|---|---|
| 58 | 979[1] | 13 | 400 | 300 | 0.49 | 34.2 | 3.1 | 78.6 | 18.3 |
| 59 |  |  |  | 325 | 0.53 | 47.2 | 1.0 | 28.4 | 7.9 |
| 60 | 980[1] | 13 | 375 | 300 | 0.48 | 21.8 | 6.6 | 91.2 | 26.6 |
| 61 |  |  |  | 325 | 0.48 | 40.8 | 1.8 | 53.1 | 14.0 |
| 62 | 970[1] | 13 | 100 | 300 | 0.50 | 10.7 | 14.0 | 100.0 | 26.1 |
| 63 |  |  |  | 325 | 0.46 | 35.7 | 2.9 | 70.8 | 15.8 |
| 64 | 980-25[1] | 25 | 325 | 300 | 0.47 | 18.2 | 12.9 | 100.0 | 19.2 |
| 65 |  |  |  | 325 | 0.50 | 42.4 | 3.3 | 68.4 | 7.8 |
| 66 | T-1219[2] | ? | 102 | 300 | 0.49 | 17.7 | 14.5 | 94.1 | 17.7 |
| 67 |  |  |  | 325 | 0.50 | 40.8 | 3.7 | 67.1 | 8.5 |

[1]Davison silica-alumina.
[2]UCI silica-alumina.

TABLE 12

| Ex. | EDA/MEA (moles) (1) | Temp., °C. | SV | % Total Conv. | DETA PIP | % NC, TETA | % AEEA |
|---|---|---|---|---|---|---|---|
| 68 | 1.00 | 275 | 0.47 | 6.1 | 33.0 | — | 19.0 |
| 69 | 1.00 | 300 | 0.47 | 18.2 | 12.9 | 100.0 | 19.2 |
| 70 | 1.00 | 310 | 0.50 | 20.5 | 10.6 | 95.8 | 18.8 |
| 71 | 1.00 | 315 | 0.50 | 23.5 | 8.7 | 87.9 | 16.3 |
| 72 | 1.00 | 318 | 0.46 | 28.2 | 7.1 | 84.4 | 15.1 |
| 73 | 1.00 | 324 | 0.50 | 42.4 | 3.3 | 68.4 | 7.8 |
| 74 | 1.00 | 322 | 0.49 | 34.0 | 5.2 | 80.0 | 12.3 |

(1) Reaction in the presence of Davison catalyst, Grade 980-25.

TABLE 13

| Ex. | Catalyst age, hrs. (1) | Temp., °C. | Press., psig | SV | % Total Conv. | DETA PIP | % NC, TETA | % AEEA |
|---|---|---|---|---|---|---|---|---|
| 75 | 18.0 | 324 | 1516 | 0.50 | 42.4 | 3.3 | 68.4 | 7.8 |
| 76 | 149.5 | 324 | 2600 | 0.48 | 24.0 | 12.0 | 91.7 | 21.3 |
| 77 | 155.5 | 324 | 1500 | 0.50 | 23.9 | 10.6 | 94.1 | 21.9 |

(1) Davison silica-alumina catalyst, Grade 980-25.

What is claimed is:

1. A method of preparing predominantly linear polyethylenepolyamines from ethyleneamines and alkanolamines, which comprises:

mixing and reacting about one-half mole to about five moles of ethyleneamine per mole of alkanolamine with an alkanolamine at a temperature of about 250° C. to about 400° C. and a pressure of about 500 to about 5000 psig in the presence of about 0.01 to about 20.0 weight percent of a silica-alumina catalyst and about 0.1 to about 3.0 weight percent of a phosphorus acid co-catalyst; and recovering a polyethylenepolyamine product characterized by a relatively large percentage of linear, noncyclic polyethylenepolyamines.

2. The method of claim 1, wherein the ethyleneamine is ethylenediamine.

3. The method of claim 1, wherein the alkanolamine is monoethanolamine.

4. A method of preparing predominantly linear polyethylenepolyamines from ethyleneamines and alkanolamines, which comprises:

mixing and reacting about one-half mole to about two moles of ethyleneamine per mole of alkanolamine with alkanolamine at a temperature of about 275° C. to about 325° C. and a pressure of about 1000 to about 3000 psig in the presence of about 2.5% to about 6.0% by weight of a pelleted silica-alumina catalyst and about 0.1% to about 3% by weight of a phosphorous acid cocatalyst, based on the amount of alkanolamine present; and recovering a polyethylenepolyamine product characterized by a relatively large percentage of linear, noncyclic polyethylenepolyamines.

* * * * *